(12) United States Patent
Meyer et al.

(10) Patent No.: US 6,302,579 B1
(45) Date of Patent: Oct. 16, 2001

(54) MULTIPLE EXAMINATION ARRANGEMENT WITH A NUMBER OF IMAGING SYSTEMS

(75) Inventors: Michael Meyer, Baiersdorf; Hans-Peter Seubert, Heroldsbach, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/441,073

(22) Filed: Nov. 16, 1999

(30) Foreign Application Priority Data

Nov. 19, 1998 (DE) .............................. 198 53 463

(51) Int. Cl.[7] ..................................................... A61B 5/00
(52) U.S. Cl. .......................... 378/196; 378/195; 378/20; 600/411
(58) Field of Search ............................... 378/20, 193, 195, 378/196, 197, 198, 204, 208, 209; 600/411, 427

(56) References Cited

U.S. PATENT DOCUMENTS

| 5,133,338 | * | 7/1992 | Wess et al. ....................... 378/195 X |
| 5,329,567 | * | 7/1994 | Ikebe ....................................... 378/20 |
| 5,661,772 | | 8/1997 | Bär et al. . |
| 5,818,901 | | 10/1998 | Schulz . |

FOREIGN PATENT DOCUMENTS 0 205 689    12/1986 (EP) .

* cited by examiner

*Primary Examiner*—David P. Porta
(74) *Attorney, Agent, or Firm*—Schiff Hardin & Waite

(57) ABSTRACT

A multiple examination arrangement has a number of imaging systems, including at least an angiography system, a CT system and an MR system arranged in a room such that a patient lying on a patient bearing table can be selectively examined without repositioning in one of the imaging systems by a relative movement of the carrier of the imaging systems and the patient support table.

7 Claims, 5 Drawing Sheets

MULTIPLE EXAMINATION ARRANGEMENT WITH A NUMBER OF IMAGING SYSTEMS

BACKGROUND OF THE INVENTION

1. Field of the Invention

The present invention is directed to a multiple examination arrangement with a number different of imaging systems.

2. Description of the Prior Art

Different imaging modalities, such as MR examinations, CT examinations or angiography examinations, can be carried out at a patient in order to diagnose pathological conditions. Usually, these different systems are accommodated in different rooms, or even different departments of a hospital. This makes the examination of a patient more difficult and complicated when, for example after a radiographic examination, a magnetic resonance examination or a computed tomography examination is also necessary for a more exact diagnosis.

It has been proposed, for example, in U.S. Pat. No. 5,661,772 to combine an X-ray device with a computed tomography device arranged next to it such that the patient can be moved through both systems on a patient support table. This known system, however, is not appropriate for multiple examinations with three or more devices. Moreover, when a patient is being examined in one of these imaging systems, all other systems are blocked and cannot be utilized.

SUMMARY OF THE INVENTION

An object of the present invention is to provide a multiple examination arrangement of the type described above wherein a patient can be more rapidly subjected to different examination modalities and wherein the examination systems thus are more optimally employed loaded to capacity.

The above object is achieved in a multiple examination arrangement wherein all imaging systems, including at least an angiography system, a CT system and an MR system, are arranged in a room on a carrier so that a patient lying on a patient support table can be selectively examined in any one of the imaging systems without repositioning the patient, by a relative movement of the carrier of the imaging systems and the patient support table.

In an embodiment of the inventive multiple examination arrangement, the imaging systems each have an insertion axis that is radially outwardly directed and are arranged on a common, movable carrier, which is opposite a patient support table that is stationarily arranged, and wherein the carrier is a rotary table or a longitudinal carriage or a displacement platform.

Due to the usually strong mechanical loads and oscillations of the imaging systems, it can thereby be provided in a further embodiment of the invention these imaging systems in the different orientation positions relative to the stationary patient support table, can be additionally braced and locked relative to the fixed floor of the room by releasable interlock elements. This means that lower requirements exist concerning the fashioning and the oscillation damping of the movable carrier, since the actual holding device for the imaging system currently in use is effected by the additional stationary detents in the examination positions.

It is also possible in accordance with the invention to arrange, along the displacement path of the carrier, a number of patient support tables for use by the imaging systems at the same time.

In a second embodiment of the invention, the imaging systems that are stationarily arranged on a circular arc each having an inwardly radially directed insertion axis and a patient support table is rotatable around the center of the circular arc, preferably on a rotary annular table. In this embodiment, the imaging systems can be connected to the floor of the examination room in a rigid and oscillation-damped manner. The rotary table for the selective positioning of the patient support table in front of the insertion opening of one of the imaging systems can be fashioned far more simply than the rotary table or the displacement platform with the imaging systems arranged thereon. There is the possibility, by means of a patient support table that can be moved on rollers, to use the remaining imaging systems so that, in a manner conforming to conventional imaging systems, the patient can be inserted from the outside into the imaging system.

In all embodiments, it has been proven to be expedient to group the imaging systems such that a displacement of their carrier or the rotatable patient support table into a selected position is possible in which the patient support table is freely accessible as a treatment table, particularly as an operation table.

DESCRIPTION OF THE PREFERRED EMBODIMENTS

Figure 1:
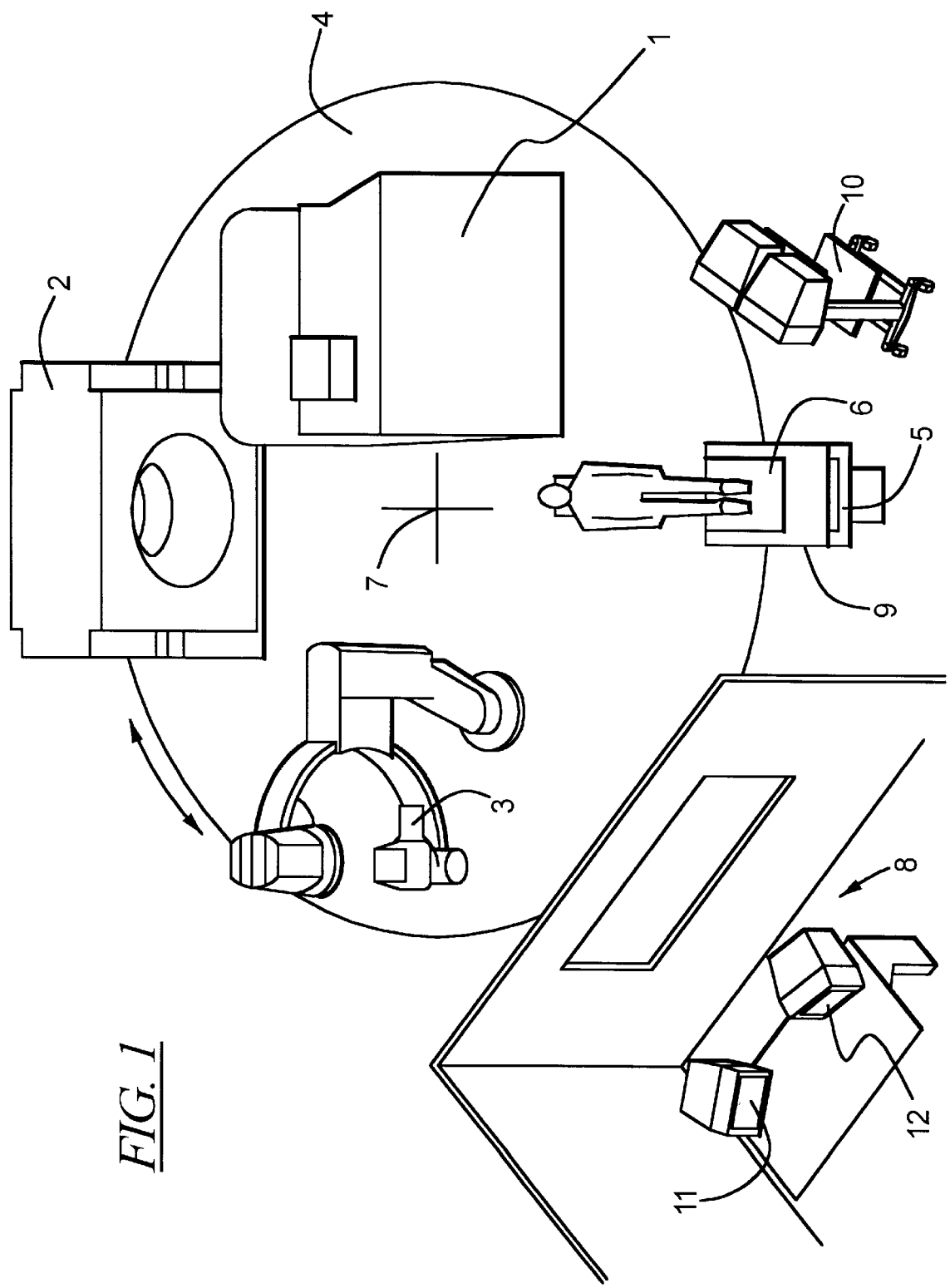
FIG. 1 is a view of a first embodiment of an inventive multiple examination arrangement with imaging systems arranged on a rotary table.

FIG. 1 shows a multiple examination arrangement wherein, in a room, different imaging systems, which are an MR system 1, an CT system 2 and an angiography system 3 in the shown exemplary embodiment, are arranged on a common rotary table 4 so that their respective insertion directions are radially outwardly directed. By means of the rotary table 4, the different imaging systems 1, 2 and 3 can be placed into a position opposite a stationarily arranged patient support table 5 that has a movable table top.

The rotary table 4 can be rotated around its center 90° to the right and 180° to the left in order to avoid difficulties given current supply and tapping of the signals from the different imaging systems—wipers would be extremely disturbing for such purposes. Thus, apart from the shown position in which the patient is freely accessible from all sides and, for example, in which the patient also can be operated on, rotary positions are possible wherein the patient on the stationary patient support table 5 can be selectively inserted into one of the imaging systems. The type of examination can be determined within a control room 8 in which different monitors 11 and 12 are arranged or can be directly set by an operator control panel 9 at the patient support table 5. The display of the examined body region ensues at the monitor carriage 10 or at the monitors 11 and 12 in the control room.

Figure 2:
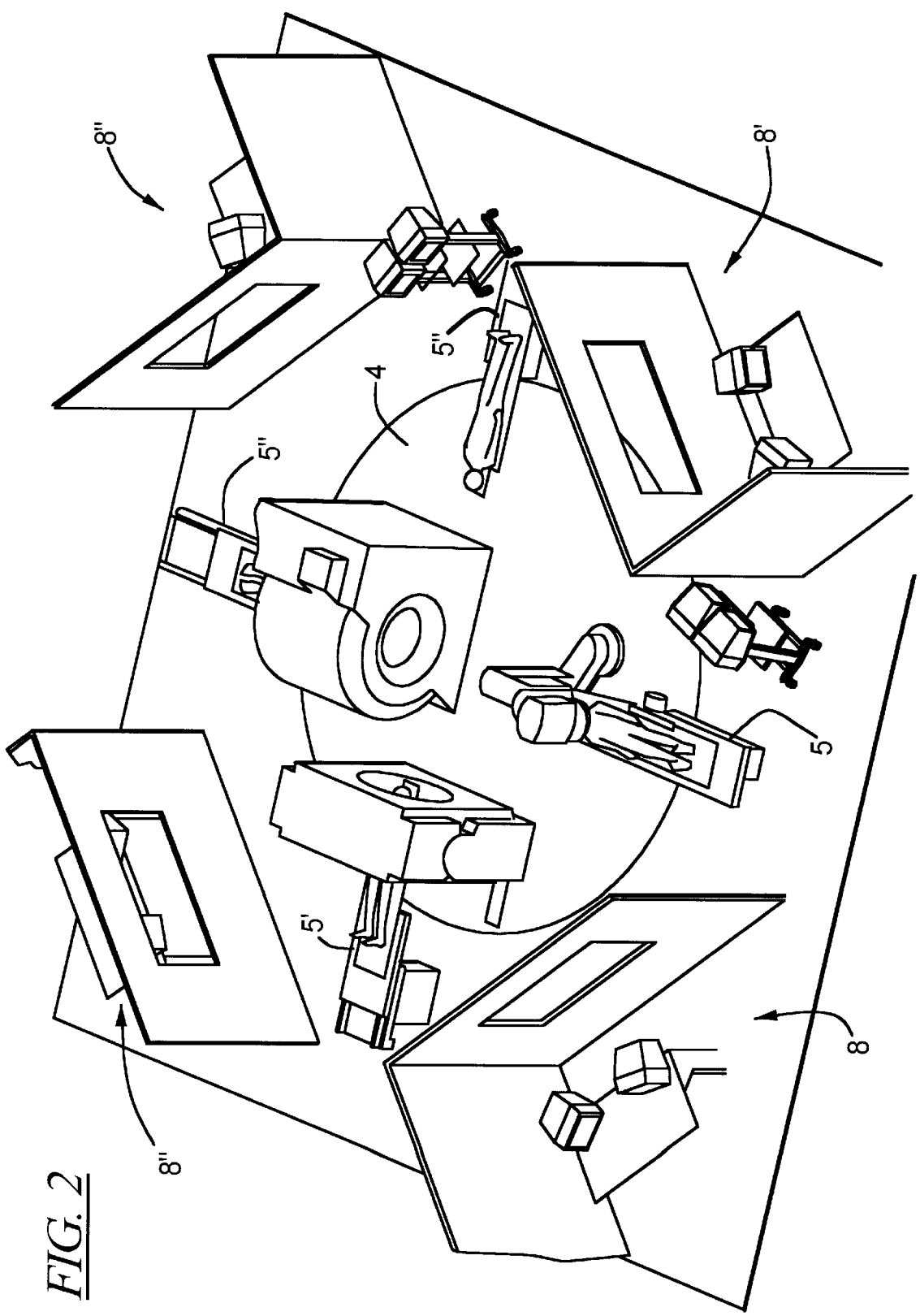
FIG. 2 shows a version of the multiple examination arrangement according to FIG. 1 with the additional possibility of using all systems at the same time and to use each imaging system with any of a number of patient support tables.

FIG. 2 shows the same rotary table 4 with the imaging systems as shown in FIG. 1. Differing from the arrangement according to FIG. 1, a number of patient support tables 5, 5', 5" and 5''' are arranged at each system, so that the usage of the individual systems can be increased allowing a number of patients to be examined at the same time. In this case, correspondingly more control rooms 8, 8', 8", 8''', as warranted, in the form of cabins in the examination room or as rooms that are grouped around the examination room, are provided.

In the multiple examination arrangements according to the FIGS. 1 and 2 with imaging systems disposed on a rotary table, (in a manner not shown) additional lock elements respectively firmly brace the imaging system to the floor of the examination room are located under the rotary table in positions directed toward the respective patient support tables 5, 5', 5", 5''' in order to be able to damp the strong oscillations that particularly occur given MR devices and CT devices.

Figure 3:
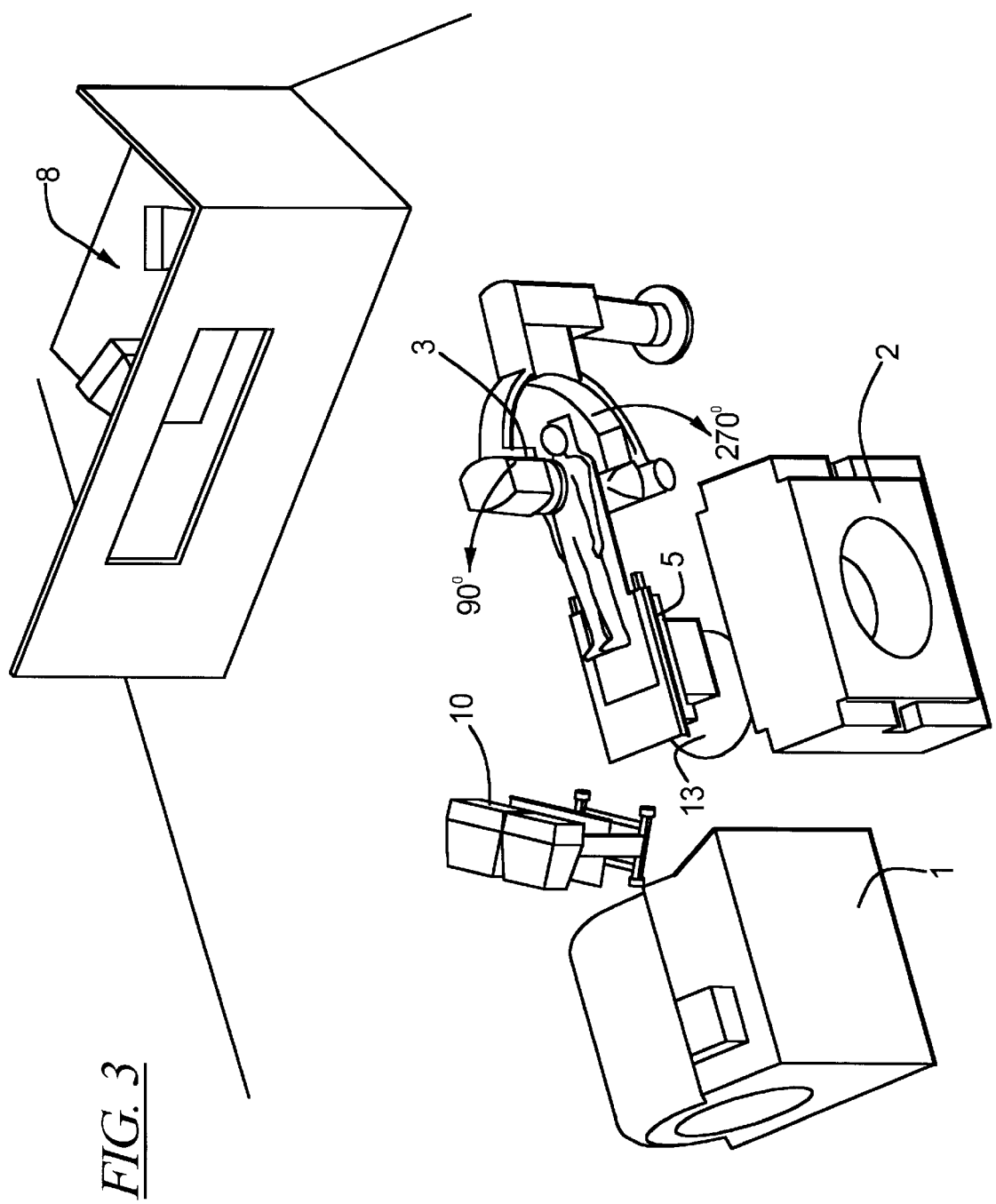
FIG. 3 is a schematic view of a multiple examination arrangement with stationarily arranged imaging systems around a patient support table that can be rotated on a rotary table.

In the exemplary embodiment according to FIG. 3, the patient support table 5 is arranged on a rotary table 13 and the different imaging systems 1, 2 and 3 are grouped on a circular arc around the rotation point of the rotary table 13. The grouping is designed such that an additional position exists wherein the patient on the patient support table 5 is freely accessible from all sides. This is the position wherein the patient bearing table is moved 90° to the left, proceeding from the position in FIG. 3.

Figure 4:
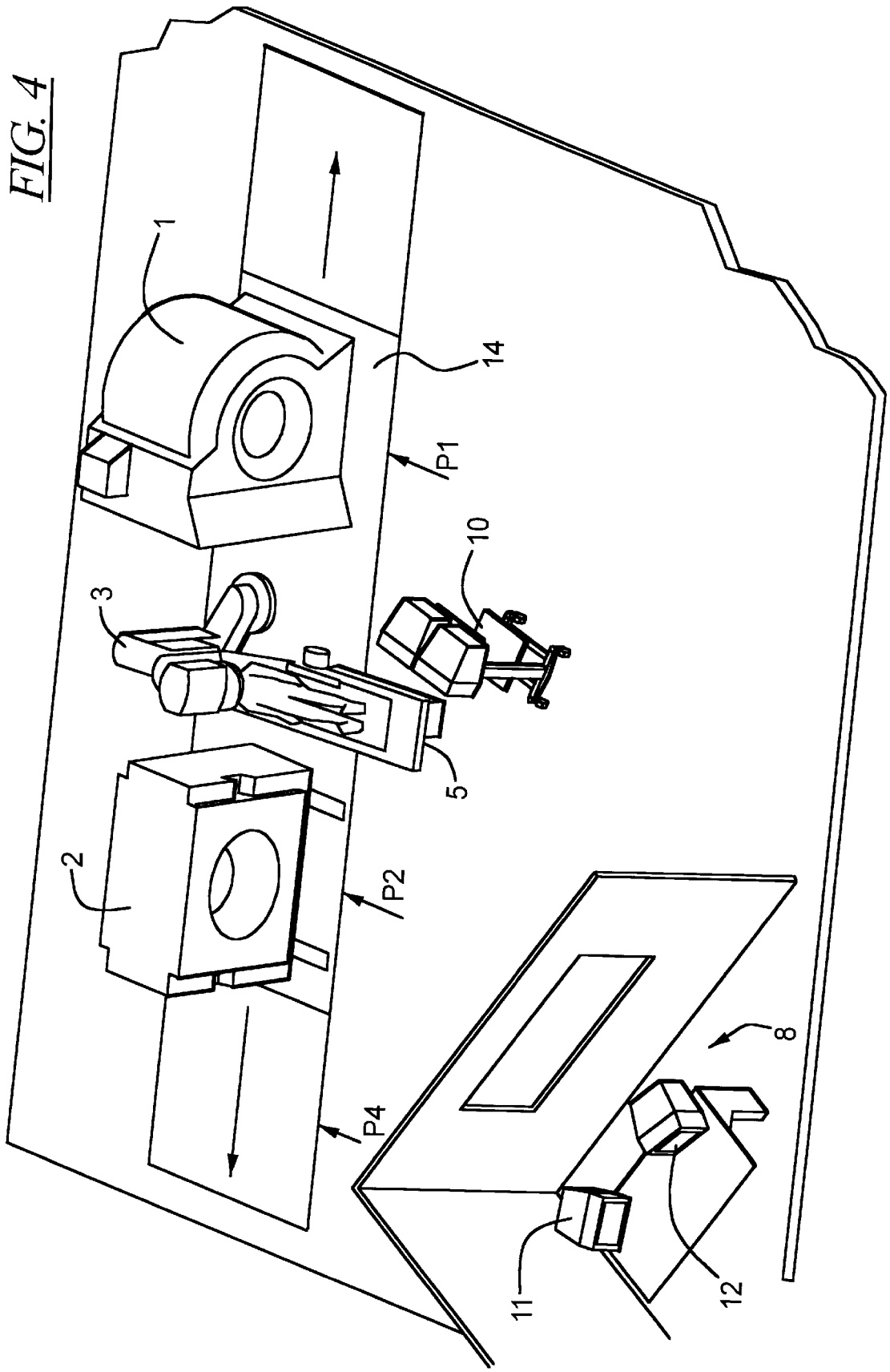
FIG. 4 shows an inventive multiple examination arrangement wherein the imaging systems are displaceable on a displacement platform relative to the stationary patient support table.
Figure 5:
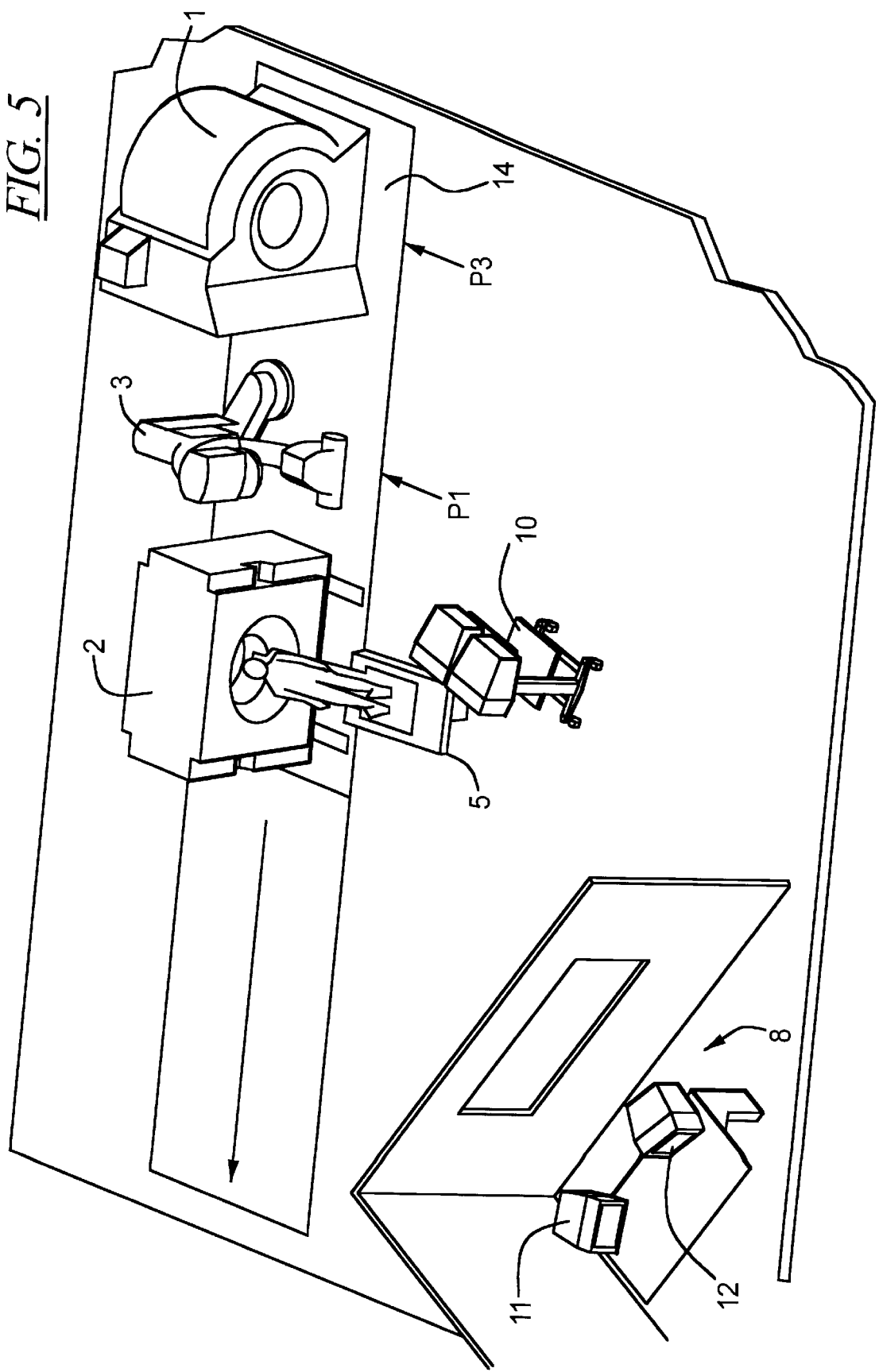
FIG. 5 is a view of the multiple examination system according to FIG. 4 in a different displacement position of the displacement platform.

In the exemplary embodiment of an inventive multiple examination arrangement shown in the FIGS. 4 and 5, the imaging systems 1, 2 and 3 are arranged on a displacement platform 14, so that they can be selectively positioned in front of the stationary, non-rotatable patient support table 5 by a linear movement. Instead of a displacement platform, a longitudinal carriage could be used. In all of these embodiments additional lock elements are provided in order to additionally connect the imaging systems to the fixed floor under the longitudinal carriage or the displacement platform 14 in the working position in front of the patient support table 5. The longitudinally displaceable fashioning of a carrier for the different imaging systems according to the FIGS. 4 and 5 also enables a better usage of the individual systems because a number of patients can be examined at the same time. These patients would are at additional stations that are arranged in the positions P1 through P4.

The invention is not limited to the shown exemplary embodiments. Apart from the possibility of the arrangement of further imaging systems, for example the arrangement of an ultrasound device, on the common carrier, or around the rotatable patient support table, it would also be possible, in the case of the longitudinally displaceably arranged imaging systems according to the FIGS. 4 and 5, to provide guide rails on which the imaging systems 1, 2 and 3 are individually movable, instead of providing a displacement platform or a longitudinal carriage. In this case, it would be particularly important to provide additional locks for the individual carriages of the imaging systems 1, 2 and 3 for the oscillation-damped connection to the fixed floor, in the respective working positions of the patient support table.

Although modifications and changes may be suggested by those skilled in the art, it is the intention of the inventors to embody within the patent warranted hereon all changes and modifications as reasonably and properly come within the scope of their contribution to the art.

We claim as our invention:

1. An examination arrangement comprising:

a plurality of medical imaging systems including at least an angiography system, a computed tomography system and a magnetic resonance imaging system;

a stationarily mounted patient support table having at least one movable element adapted to receive an examination subject thereon;

each of said imaging systems having an insertion axis along which said at least one movable element of said patient support table is movable into the respective imaging system; and a common carrier on which all of said imaging systems are mounted, said carrier being movable relative to said patient support table to bring the insertion axis of a selected one of said imaging systems into substantial alignment with said at least one movable element of said patient support table.

2. An examination arrangement as claimed in claim 1 wherein said carrier comprises a rotary carrier, and wherein the respective insertion axes of said imaging systems are directed radially outwardly from a center of said rotary carrier.

3. An examination arrangement as claimed in claim 1 wherein said carrier comprises a longitudinal carriage, and wherein the respective insertion axes of said imaging systems are disposed parallel to a direction of movement of said at least one movable element of said patient support table.

4. An examination arrangement as claimed in claim 1 for use in an examination room having a floor, and wherein said examination arrangement further comprises a bracing and locking arrangement for releasably fixing said carrier to said floor with a selected one of said imaging systems aligned with said stationary patient support table.

5. An examination arrangement as claimed in claim 1 further comprising a plurality of additional patient support tables, each having at least one movable element adapted to receive an examination subject thereon, each of said additional patient support tables being stationarily mounted relative to said carrier, and said patient support table and said plurality of additional patient support tables being disposed relative to said carrier for simultaneous use of more than one of said imaging systems.

6. An examination arrangement as claimed in claim 5 wherein said imaging systems are disposed on said carrier so as to leave a gap between two of said imaging systems, wherein said patient support table is freely accessible as a treatment table.

7. An examination arrangement comprising:

a plurality of medical imaging systems including at least an angiography system, a computed tomography system and a magnetic resonance imaging system, said medical imaging systems being respectively stationarily disposed on a circular arc having a center;

a patient support table having at least one movable element adapted to receive an examination subject thereon, said at least one movable element being rotatable around said center; and each of said imaging systems having an insertion axis along which said at least one movable element of said patient support table is movable into the respective imaging system, the respective insertion axes being directed radially inwardly toward said center.

* * * * *